(12) United States Patent
Feld et al.

(10) Patent No.: US 6,941,953 B2
(45) Date of Patent: Sep. 13, 2005

(54) PREFORMED CATHETER SET FOR USE WITH A LINEAR ABLATION SYSTEM TO PRODUCE ABLATION LINES IN THE LEFT AND RIGHT ATRIUM FOR TREATMENT OF ATRIAL FIBRILLATION

(75) Inventors: Gregory K. Feld, Rancho Santa Fe, CA (US); Theodore C. Ormsby, Milpitas, CA (US); Ming-Fan Law, San Diego, CA (US); George L. Leung, San Diego, CA (US)

(73) Assignee: Medwaves, Inc., San Diego, CA (US)

( * ) Notice: Subject to any disclaimer, the term of this patent is extended or adjusted under 35 U.S.C. 154(b) by 68 days.

(21) Appl. No.: 10/772,861

(22) Filed: Feb. 6, 2004

(65) Prior Publication Data

US 2004/0167510 A1 Aug. 26, 2004

Related U.S. Application Data

(60) Provisional application No. 60/449,097, filed on Feb. 20, 2003.

(51) Int. Cl.[7] .............................................. A61N 19/00
(52) U.S. Cl. .......................... 128/898; 606/41; 607/122
(58) Field of Search ........................... 128/898; 606/41, 606/45–50; 607/101, 102, 116, 122; 600/372, 374

(56) References Cited

U.S. PATENT DOCUMENTS

| | | | | |
|---|---|---|---|---|
| 5,617,854 A | * | 4/1997 | Munsif | 600/374 |
| 5,642,736 A | * | 7/1997 | Avitall | 600/585 |
| 6,033,403 A | * | 3/2000 | Tu et al. | 606/41 |
| 6,237,605 B1 | | 5/2001 | Vaska et al. | |
| 6,319,250 B1 | * | 11/2001 | Falwell et al. | 606/41 |
| 6,527,769 B2 | * | 3/2003 | Langberg et al. | 606/41 |
| 6,592,581 B2 | * | 7/2003 | Bowe | 606/41 |
| 2002/0165533 A1 | * | 11/2002 | Flores | 606/41 |

* cited by examiner

Primary Examiner—Michael Peffley
(74) Attorney, Agent, or Firm—Procopio Cory Hargreaves & Savitch

(57) ABSTRACT

A preformed catheter set for production of linear ablation lines in the left and right atrium for treatment of atrial fibrillation includes at least a first catheter including a pre-shaped distal segment having a distal linear ablation antenna and a U-shaped curve portion proximal to the distal linear ablation antenna.

7 Claims, 6 Drawing Sheets

PREFORMED CATHETER SET FOR USE WITH A LINEAR ABLATION SYSTEM TO PRODUCE ABLATION LINES IN THE LEFT AND RIGHT ATRIUM FOR TREATMENT OF ATRIAL FIBRILLATION

CROSS-REFERENCE TO RELATED APPLICATION

This application claims the benefit of prior provisional application No. 60/449,097, filed Feb. 20, 2003, under 35 U.S.C. 119(e).

FIELD OF THE INVENTION

This invention relates generally to radio-frequency ("RF") or microwave powered medical apparatus and ablation of biological tissues. More particularly, this invention concerns a preformed catheter set for treatment of atrial fibrillation.

BACKGROUND OF THE INVENTION

References are made of U.S. Pat. No. 6,190,382, issued on Feb. 20, 2001, and U.S. patent application Ser. No. 10/306,757, filed with the United States Patent and Trademark Office on Nov. 27, 2002 and entitled: "Radio-Frequency-based Catheter System with Improved Deflection and Steering Mechanisms," which include the same inventors as the present application and are incorporated hereto in full by reference.

Cardiac arrhythmias are a major cause of morbidity and mortality in humans, especially atrial fibrillation. Atrial fibrillation may affect up to 10% of the population by the 7th or 8th decade of life, and is responsible for tens of thousands of hospitalizations each year at a cost of over a billion dollars. Extensive research in the past decade has shown that atrial fibrillation is due to electrical reentry phenomenon in the atria, causing a rapid depolarization of the tissue at rates of 350–500 beats per minute. The rapid electrical depolarization causes inadequate contraction, which can lead to stasis of blood with clot formation that can cause a stroke, the single most debilitating and life threatening complication of atrial fibrillation. The risk of stroke can be reduced by anticoagulation, but is not eliminated. In addition, the rapid ventricular response caused by atrial fibrillation can lead to congestive heart failure, another significant cause of morbidity and mortality in patients with atrial fibrillation. Finally, atrial fibrillation causes debilitating symptoms in a majority of patients. Atrial fibrillation can be controlled with antiarrhythmic medications, but only about 50% of patients respond. Another option for treatment is pacemaker implantation, with or without ablation of the AV node for rate control, but this does not reduce the risk of stroke, nor relieve symptoms in all patients. Consequently, since current therapies are inadequate to prevent recurrence of atrial fibrillation in a majority of patient, alternative approaches to curing atrial fibrillation have been sought.

Atrial fibrillation, in its paroxysmal stage, has been shown to be triggered by focal premature electrical depolarizations in the pulmonary veins, which can be cured by electrical isolation of the pulmonary veins from the left atrium using limited map-guided radio-frequency catheter ablation. However, this approach is only effective in approximately 70–80% of patients with paroxysmal atrial fibrillation, and in fewer than 20% of patients with chronic or persistent atrial fibrillation. In addition, ablation in or around the pulmonary veins may cause their stenosis in a small percentage of cases, a serious and potentially life-threatening complication.

A more extensive ablation procedure is required in patients with persistent atrial fibrillation, which is to interrupt all potential reentrant electrical circuits in the atria. One such procedure is commonly known as the MAZE operation. Maze operation is applied to block potential reentrant electrical activation in the right and left atria, while allowing conduction from the sinus node to the AV node through a maze-like pathway and normal AV conduction and AV synchrony to persist following cure of atrial fibrillation. However, this procedure must be done as an open-heart surgery, typically while the patient is on cardiopulmonary bypass. This type of surgery is associated with significant potential morbidity and a mortality rate of 2–5%. Therefore, since most patients are reluctant to undergo such an invasive procedure, and their overall medical condition may prohibit them from taking the risks associated with such a procedure, a less invasive approach is desirable.

Various radio-frequency catheter ablation techniques have been applied for curing many atrial arrhythmias. These include supraventricular tachycardia, atrial flutter and more recently focal triggered paroxysmal atrial fibrillation. These techniques have also been attempted for treatment of persistent atrial fibrillation. Multiple focal lesions can be placed to form linear ablation lesions surrounding the pulmonary veins in the left atrium with a line anchoring this set of lesions to the mitral valve annulus, alone or in combination with a set of linear lesions in the posterior and septal right atrium and sub-Eustachian isthmus (i.e., so called flutter line). Linear ablation using such techniques has been shown to be effective in up to 70% of patients in some studies, but continued treatment with antiarrhythmic medications is often required. In addition, the occurrence of incomplete lines of ablation effected by multiple focal lesions is common, resulting in a high risk of recurrent reentrant atrial tachycardia thus, requiring further ablation. Furthermore, because of the prolonged procedure time required to complete the ablation using this multiple focal lesions approach, there is up to a 5% risk of embolic stroke and other serious complications.

As referenced in U.S. Pat. No. 6,190,382 and U.S. patent application Ser. No. 10/306,757, effective treatments for atrial fibrillation with catheter ablation requires the creation of long or overlapping lineal or curvilinear ablation lesions on the inner surface of the atrium. These lesions can then act as barriers to the conduction of electrical impulses, thus preventing atrial fibrillation.

U.S. Pat. No. 6,190,382 and U.S. patent application Ser. No. 10/306,757, disclose a radio-frequency or microwave-energy based catheter for ablating biological tissues within the body vessel of a patient. The catheter has a proximal portion, a distal portion with a distal end and a lumen extending from the proximal portion to the distal portion. The catheter incorporates an elongated catheter guide that is located within the catheter lumen and is secured to the distal portion of the catheter at one end, with the other end portion extending proximally within the catheter lumen to be coupled to a positioning mechanism. A significant advantage of the catheter guide is that it is deployable beyond the distal end of the catheter to form a loop, which is conformable to the interior contour of the body vessel. The catheter guide carries the catheter with a radio-frequency or microwave energy based antenna incorporated at the distal portion of the catheter. The antenna includes a helical coil, which accommodates the catheter guide passing through it. The radio-frequency antenna is adapted to receive and irradiate radio-frequency energy in the microwave range at a frequency typically greater than 300 Megahertz (MHz) in the electromagnetic spectrum for ablating biological tissue along a biological ablation pathway.

SUMMARY OF INVENTION

The present invention provides further enhancements and features to the catheters described in U.S. Pat. No. 6,190,382 and U.S. patent application Ser. No. 10/306,757. These improvements and features, among others, include pre-shaped and shapeable portions and antenna at the distal end portions of the catheters and methods of use. The improved catheters can incorporate the steerable features as disclosed in U.S. Pat. No. 6,190,382 and U.S. patent application Ser. No. 10/306,757, to effect a set of steerable pre-shaped catheters, which enables completion of a linear ablation procedure in the left and right atrium more effectively and in a much shorter time than current standard radio-frequency catheter ablation techniques. The improvements enables a greater success rate and lower complication rate for the cure of atrial fibrillation.

The catheters allow the physician operator to produce a set of four left atrial linear lesions surrounding the pulmonary veins. The first lesion is connected to the mitral valve annulus, followed by a set of three right atrial lesions, which connect the superior vena cava and inferior vena cava via a posterior line, the superior vena cava and foramen ovale via a septal line, and the tricuspid valve annulus and inferior vena cava via an isthmus line.

A pre-shaped left atrial catheter set comprises three distal catheter shapes (i.e., #1, 2, and 3, as shown in FIGS. 3, 4 and 5, respectively) enables complete electrical isolation of the pulmonary veins from the surrounding left atrium to prevent focal triggering of atrial fibrillation and reentry around the pulmonary veins and mitral valve annulus. A right atrial lesion set can be created using catheter shape #1 from the left atrial pre-shaped catheter set, and a fourth (#4, FIG. 6) design shape specifically for the TV-IVC isthmus ablation.

The pre-shaped catheters incorporate unique pre-shaped distal segments. These segments can be formed as parts of the catheters shown in U.S. Pat. No. 6,190,382 and U.S. patent application Ser. No. 10/306,757. The catheters are self-positioning with minimal manipulation by the physician operator. When placed in the left (via transeptal puncture) and right atrium respectively, the catheters allow ablation in specific pre-determined locations to best achieve ablation for atrial fibrillation, achieving a so-called catheter "MAZE" operation. The resultant lesion sets, achieved with the use of this invention, are shown in FIGS. 1 & 2.

In an aspect of the invention, the preformed catheter set for production of linear ablation lines in the left and right atrium for treatment of atrial fibrillation includes at least a first catheter including a pre-shaped distal segment having a distal linear ablation antenna and a U-shaped curve portion proximal to the distal linear ablation antenna. In an implementation of this aspect of the invention, the catheter set is a pre-shaped left atrial catheter set to provide complete electrical isolation of the pulmonary veins from the surrounding left atrium to prevent focal triggering of atrial fibrillation and reentry around the pulmonary veins and mitral valve annulus, the U-shaped curve of the first catheter allows catheter contact with a posterior wall of the left atrium horizontally just superior or just inferior to pulmonary veins, and the catheter set further includes a second catheter including a pre-shaped distal segment having a distal linear ablation antenna and a 90° deflected portion proximal to the linear ablation antenna; and a third catheter including a pre-shaped distal segment having a distal linear ablation antenna and a 170–180° deflected portion proximal to the linear ablation antenna. In another implementation of this aspect of the invention, the catheter set is a pre-shaped right atrial catheter set to provide TV-IVC isthmus ablation, and the catheter set further includes a second catheter including a pre-shaped distal segment having a distal linear ablation antenna and a 45–60° deflected portion proximal to the linear ablation antenna.

Another aspect of the invention involves a method of producing linear ablation lines in the left and right atrium for treatment of atrial fibrillation. The method includes providing a preformed catheter set including at least a first catheter including a pre-shaped distal segment having a distal linear ablation antenna and a U-shaped curve portion proximal to the distal linear ablation antenna; deploying the preshaped distal segment in the left or right atrium so that the pre-shaped distal segment of the first catheter takes the U-shaped curve shape; and linearly ablating the atrium with the distal linear ablation antenna to treat atrial fibrillation. In an implementation of this aspect of the invention, the catheter set is a pre-shaped left atrial catheter set to provide complete electrical isolation of the pulmonary veins from the surrounding left atrium to prevent focal triggering of atrial fibrillation and reentry around the pulmonary veins and mitral valve annulus, the U-shaped curve of the first catheter allows catheter contact with a posterior wall of the left atrium horizontally just superior or just inferior to pulmonary veins, the catheter set further includes a second catheter including a pre-shaped distal segment having a distal linear ablation antenna and a 90° deflected portion proximal to the linear ablation antenna, and a third catheter including a pre-shaped distal segment having a distal linear ablation antenna and a 170–180° deflected portion proximal to the linear ablation antenna; and the method further includes creating a first and second linear ablation lesions that connect the superior and inferior pulmonary veins horizontally with the distal linear ablation antenna of the first catheter; creating a third linear ablation lesion that connects the left pulmonary veins vertically with the distal linear ablation antenna of the second catheter; and creating a fourth linear ablation lesion that connects the right pulmonary veins vertically along the inter-atrial septum, with a continuing connecting line to the mitral valve annulus, with the distal linear ablation antenna of the third catheter, whereby the linear ablation lesions provide complete electrical isolation of the pulmonary veins from the surrounding left atrium to prevent focal triggering of atrial fibrillation and reentry around the pulmonary veins and mitral valve annulus. In another implementation of this aspect of the invention, the catheter set is a pre-shaped right atrial catheter set to provide TV-IVC isthmus ablation, and the catheter set further includes a second catheter including a pre-shaped distal segment having a distal linear ablation antenna and a 45–60° deflected portion proximal to the linear ablation antenna, and the method further includes creating a linear ablation lesion from a superior vena cava to an inferior vena cava along a crista terminalis in the posterior right atrium with the distal linear ablation antenna of the first catheter; and creating a linear ablation lesion at sub-Eustachian isthmus along its entire length with the distal linear ablation antenna of the second catheter.

Further objects and advantages will be apparent to those skilled in the art after a review of the drawings and the detailed description of the preferred embodiments set forth below.

DETAILED DESCRIPTION OF PREFERRED EMBODIMENTS

Figure 1:
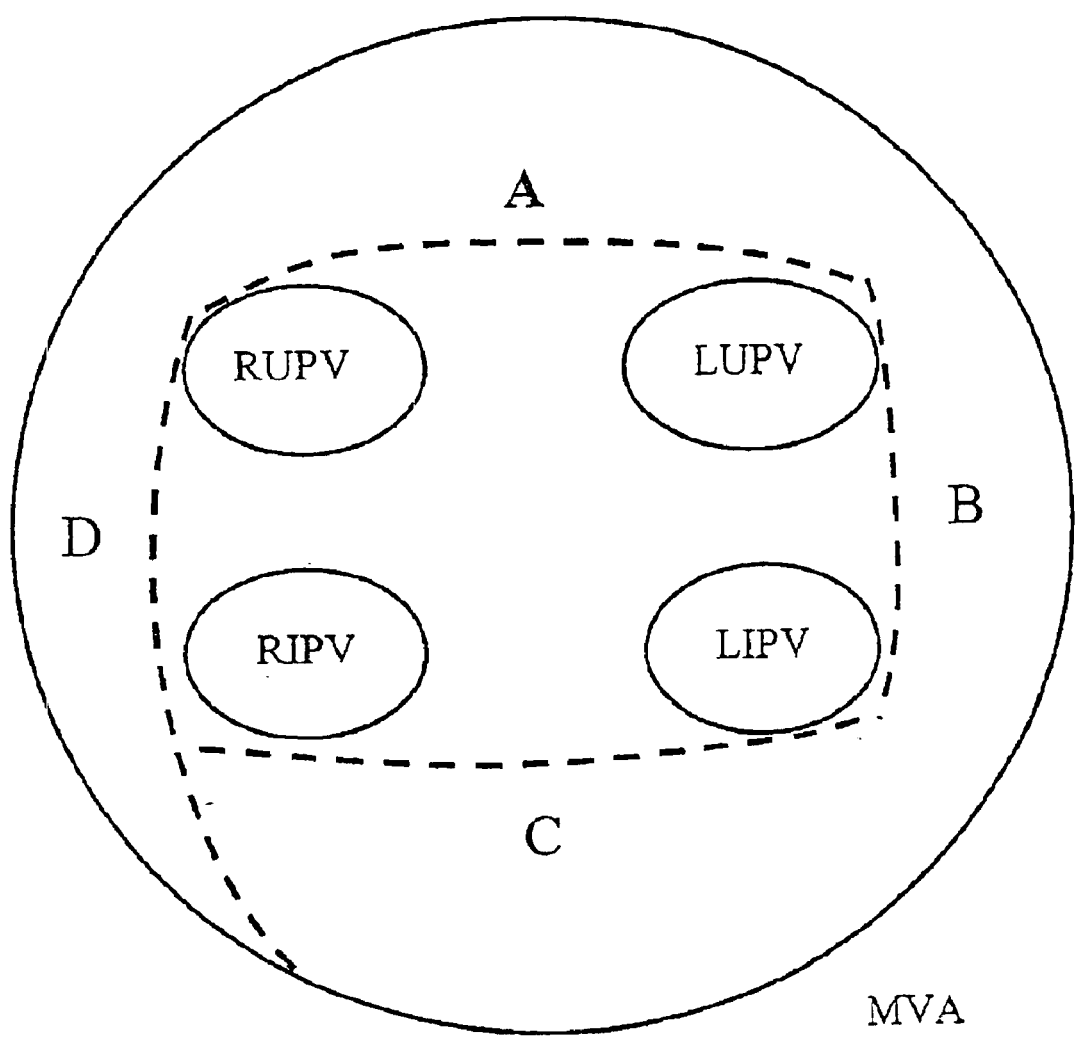
FIG. 1 is a schematic diagram of linear lesions on the left atrium for an exemplary treatment of atrial fibrillation. In the drawing, A=RUPV-LUPV lesion, B=LUPV-LIPV lesion, C=LIPV-RIPV lesion, D=RUPV-RIPV-MV annulus lesion, RUPV=right upper pulmonary vein (PV), RIPV=right inferior PV, LUPV=left upper PV, LIPV=left inferior PV, MVA=mitral valve annulus), and the dotted lines represent the linear lesions.
Figure 3:
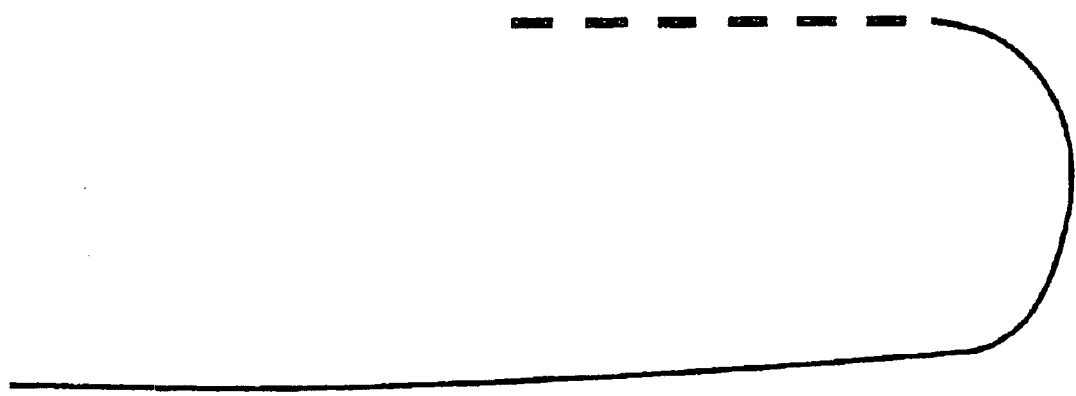
FIG. 3 is a simplified partial view of an embodiment of a deflectable and shapeable catheter shape #1 of the present invention. In the drawing, the dotted line represents the ablation antenna.
Figure 4:
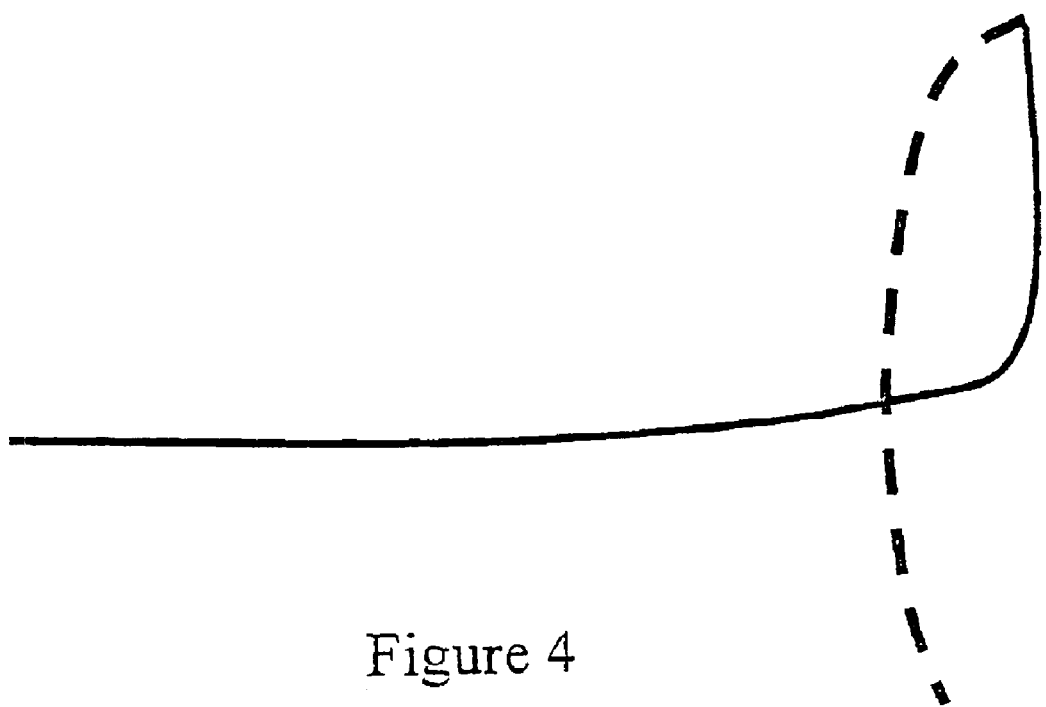
FIG. 4 is a simplified partial view of an embodiment of a deflectable and shapeable catheter shape #2 of the present invention. In the drawing, the dotted line represents the ablation antenna.
Figure 5:
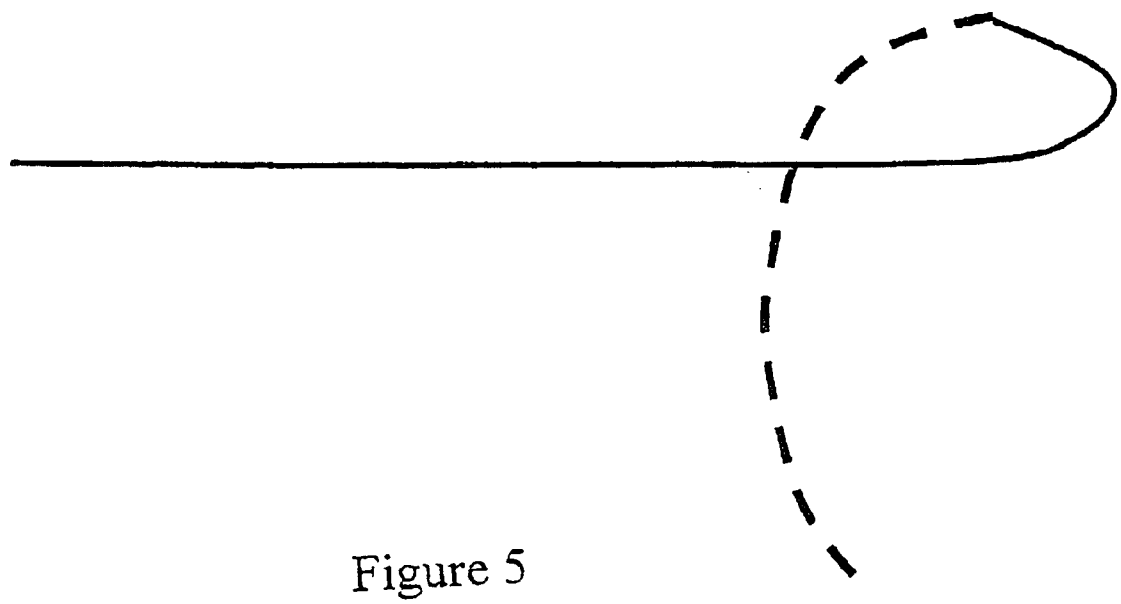
FIG. 5 is a simplified partial view of an embodiment of a deflectable and shapeable catheter shape #3 of the present invention. In the drawing, the dotted line represents the ablation antenna.

The present invention comprises pre-shaped catheter sets for left atrial linear ablation and right atrial linear ablation. In an embodiment of the pre-shaped catheter set for left atrial linear ablation, the catheter set includes three distal shapes (#1, 2, 3 as shown in FIGS. 3, 4 and 5, respectively), which are adaptable to produce four linear lesions in the left atrium as shown in FIG. 1. Catheter shape #1 is used to produce linear lesions A and C, which connect the superior and inferior pulmonary veins horizontally. Catheter shape #2 is applied to produce a left atrial linear lesion B, which connects the left pulmonary veins vertically. Catheter shape #3 is applied to produce left atrial linear lesion D, which connects the right pulmonary veins vertically along the inter-atrial septum, with a continuing connecting line to the mitral valve annulus.

Figure 2:
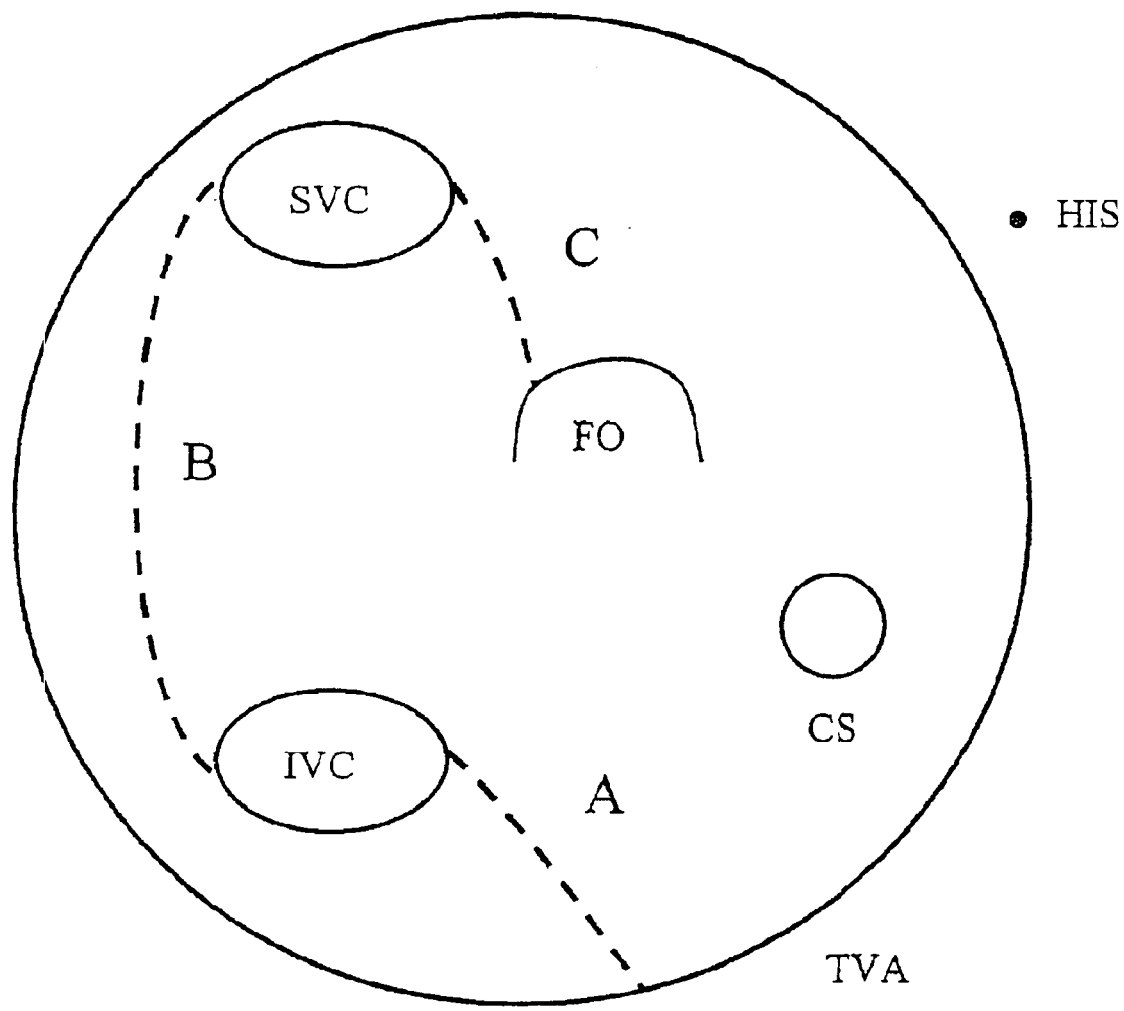
FIG. 2 is a schematic diagram of linear lesions on the right atrium for an exemplary treatment of atrial fibrillation. In the drawing, A=TV-IVC isthmus lesion, B=Crista terminalis or SVC-IVC posterior lesion, C=SVC to foramen ovale or septal lesion, FO=foramen ovale, CS=coronary sinus ostium, IVC=inferior vena cava, SVC=superior vena cava, HIS=HIS bundle, TVA=tricuspid valve annulus, and the dotted lines represent the linear lesions.
Figure 6:
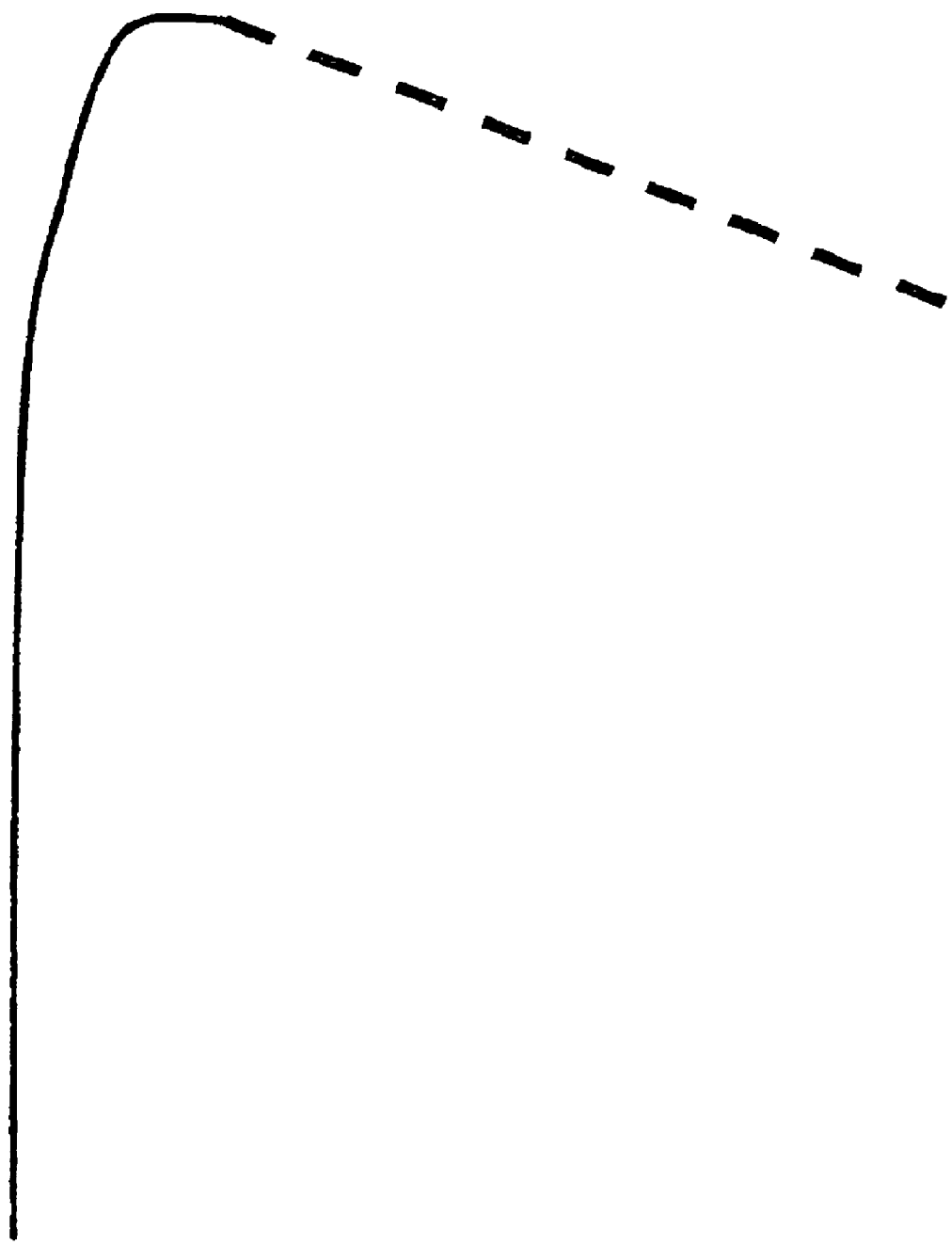
FIG. 6 is a simplified partial view of an embodiment of a deflectable and shapeable catheter shape #1 of the present invention. In the drawing, the dotted line represents the ablation antenna.

In an embodiment of the pre-shaped catheter set for right atrial linear ablation, the present invention also comprises a distal shape #4, as shown in FIG. 6, which together with catheter shape #1, defines a pre-shaped catheter set for right atrial linear ablation. This right atrial linear ablation set is adaptably applied to produce three linear lesions in the right atrium. In application, catheter shape #1 can be used to produce right atrial linear lesions B and C, as shown in FIG. 2, and catheter shape #4 can be used to produce a right atrial linear lesion A.

The size of the distal segments of the individual catheters can vary to accommodate the natural variance in left and right atrial size seen in patients with atrial fibrillation (e.g., left atrial size from 4–6 cm).

Left Atrial Lesion Set:

As shown in FIG. 3, catheter shape #1 incorporates a unidirectional deflectable curve portion of between approximately 4–6 cm in length that is proximal to the linear ablation antenna. Catheter shape #1 incorporates a U-shaped curve in the unidirectional deflectable curve portion, which allows catheter contact with the posterior wall of the left atrium horizontally just superior or just inferior to the pulmonary veins. This catheter can be retracted proximally within a transeptal sheath to reach the right pulmonary veins with the catheter tip. Alternatively, it can be advanced distally within the transeptal sheath to reach the left pulmonary veins with the proximal segment of the ablation antenna, if the linear ablation antenna is of insufficient length to span the entire horizontal line between the right and left pulmonary veins in a single ablation. The catheter shaft or handle can be rotated clockwise or counterclockwise to effect proper positioning of the linear ablation antenna to ablate the horizontal lines connecting the superior and inferior pulmonary veins.

As shown in FIG. 4, catheter shape #2 incorporates a bent or leftward, approximately at 90°, deflected portion, which is positioned 1–3 cm proximal to the distal linear ablation antenna.

The ablation antenna segment is uni-directionally deflectable. The catheter can be advanced or retracted in a transeptal sheath to reach a position just lateral to the left pulmonary veins, and rotated clockwise or counterclockwise to adjust the vertical position of the linear ablation antenna relative the left superior or inferior pulmonary vein.

FIG. 5 shows a catheter shape #3, which incorporates a bent or leftward, approximately at 170–180°, deflected portion, which is positioned 1–2 cm proximal to the distal linear ablation antenna. The ablation antenna segment is also uni-directionally deflectable toward the catheter shaft. Catheter shape #3 can also be advanced or retracted in a transeptal sheath to reach a position just lateral to the right pulmonary veins, and rotated clockwise or counterclockwise to adjust the vertical position of the linear ablation antenna relative the right superior or inferior pulmonary vein.

Right Atrial Lesion Set:

As referenced above, catheter shape #1, as shown in FIG. 3, can also be used in the right atrium, positioned via the femoral vein, catheter shape #1 can be applied to effect linear ablation from the superior vena cava to the inferior vena cava along the crista terminalis in the posterior right atrium.

This is accomplished by first deflecting the catheter into a U-shape with the distal tip of the ablation antenna at the inferior vena cava—right atrial junction, and then advancing the catheter into the femoral vein as needed during ablation until the proximal portion of the ablation antenna is at the superior vena cava—right atrial junction. In a similar manner, catheter shape #1 can be used to produce a linear ablation along the septum from the foramen ovale to the superior vena cava.

As shown in FIG. 6, catheter shape #4 incorporates a generally 45–60° deflectable portion, located approximately 1 cm proximal to the linear ablation antenna, which allows the ablation antenna segment to be oriented toward the proximal portion of the catheter. Catheter shape #4 can be positioned from the inferior vena cava by advancing the un-deflected catheter into the right atrium, and then positioning the tip of the ablation antenna at the tricuspid valve annulus, deflecting the catheter so that the ablation antenna contacts the sub-Eustachian isthmus, and then retracting the catheter from the femoral vein to create slight traction on the Eustachian ridge. This will allow the ablation antenna to maintain linear contact or in close proximity to the tissue in the sub-Eustachian isthmus along its entire length. The ablation antenna can also be positioned more medially or laterally in the sub-Eustachian isthmus by clockwise or counterclockwise rotation of the catheter shaft or handle.

Preliminary studies performed in the inventor's laboratory in the canine model have demonstrated the feasibility and safety of this invention. Using a 4 cm long microwave antenna for linear ablation, mounted on the pre-shaped catheter designs described herein, contiguous, transmural linear ablation in both the left and right atrium has been demonstrated. With this invention, as determined by non-contact balloon antenna activation mapping, complete linear ablation with isolation of the pulmonary veins has been demonstrated in the left atrium, complete linear ablation with block along the crista terminalis in the posterior right atrium has been demonstrated, and complete linear ablation of the sub-Eustachian isthmus with bidirectional conduction block has been demonstrated.

From the above description, it is apparent that the present invention does not effectively reduce, if not avoids, the need for repetitive pinpoint precision placement of the ablation catheter antenna of the prior art, but also provides substantial navigational capabilities to the catheter system for deployment within the body vessel. The present invention conveniently places the radio-frequency antenna along the locus of an antenna guide that defines the tissue ablation pathway. At the same time, the present invention ensures a continuous ablation pathway and substantially reduces the risk of electrical impulse leakage between ablated spots of the prior art. Accordingly, the present invention substantially accomplishes the objective of the Maze procedure in achieving curvilinear lesions yet without the need for open-heart surgery and with substantial reduction of time in the procedure. These and other aspects and advantages of the invention will become apparent from the following detailed description, and the accompanying drawings, which illustrate by way of example the features of the invention.

It will be readily apparent to those skilled in the art that still further changes and modifications in the actual concepts described herein can readily be made without departing from the spirit and scope of the invention as defined by the following claims.

We claim:

1. A method of producing linear ablation lines in the left atrium for treatment of atrial fibrillation, comprising:

providing a pre-shaped left atrial catheter set to provide complete electrical isolation of the pulmonary veins from the surrounding left atrium to prevent focal triggering of atrial fibrillation and reentry around the pulmonary veins and mitral valve annulus, the catheter set including a first catheter including a pre-shaped distal segment having a distal linear ablation antenna and a U-shaped curve portion proximal to the distal linear ablation antenna, the U-shaped curve of the first catheter allows catheter contact with a posterior wall of the left atrium horizontally just superior or just inferior to pulmonary veins, a second catheter including a pre-shaped distal segment having a distal linear ablation antenna and a 90° deflected portion proximal to the linear ablation antenna, and a third catheter including a pre-shaped distal segment having a distal linear ablation antenna and a 170–180° deflected portion proximal to the linear ablation antenna;

deploying the preshaped distal segment of the first catheter in the left atrium so that the preshaped distal segment of the first catheter takes the U-shaped curve shape, and creating first and second linear ablation lesions that connect the superior and inferior pulmonary veins horizontally with the distal linear ablation antenna of the first catheter;

creating a third linear ablation lesion that connects the left pulmonary veins vertically with the distal linear ablation antenna of the second catheter;

creating a fourth linear ablation lesion that connects the right pulmonary veins vertically along the inter-atrial septum, with a continuing connecting line to the mitral valve annulus, with the distal linear ablation antenna of the third catheter, whereby the linear ablation lesions provide complete electrical isolation of the pulmonary veins from the surrounding left atrium to prevent focal triggering of atrial fibrillation and reentry around the pulmonary veins and mitral valve annulus.

2. The method of claim 1, wherein the 90° deflected portion of the second catheter is positioned 1–3 cm proximal to the distal linear ablation antenna.

3. The method of claim 1, wherein the 170–180° deflected portion of the third catheter is positioned 1–2 cm proximal to the distal linear ablation antenna.

4. The method of claim 1, wherein the catheters includes a transeptal sheath and the distal segment and the transeptal sheath are relatively movable with respect to each other to deploy the distal segment, and the method further including deploying the distal segment by moving at least one of the transeptal sheath and the distal segment.

5. A method of producing linear ablation lines in the right atrium for treatment of atrial fibrillation, comprising:

providing a pre-shaped right atrial catheter set to the provide TV-IVC isthmus ablation, the catheter set including a first catheter having a pre-shaped distal segment having a distal linear ablation antenna and a U-shaped curve portion proximal to the distal linear ablation antenna, a second catheter including a pre-shaped distal segment having a distal linear ablation antenna and a 45–60° deflected portion proximal to the liner ablation antenna;

deploying the preshaped distal segment of the first catheter in the right atrium so that the preshaped distal segment of the first catheter takes the U-shaped curve shape, and creating a linear ablation lesion from a superior vena cava to an inferior vena cava along a crista terminalis in the posterior right atrium with the distal linear ablation antenna of the first catheter;

creating a linear ablation lesion at sub-Eustachian isthmus along its entire length with the distal linear ablation antenna of the second catheter.

6. The method of claim 5, wherein the 45–60° deflected portion of the second catheter is positioned 1 cm proximal to the distal linear ablation antenna.

7. The method of claim 5, wherein the catheters includes a transeptal sheath and the distal segment and the transeptal sheath are relatively movable with respect to each other to deploy the dial segment, and the method further including deploying the distal segment by moving at least one of the transeptal sheath and the distal segment.

* * * * *